US012582362B2

(12) United States Patent
Eichner et al.

(10) Patent No.: US 12,582,362 B2
(45) Date of Patent: Mar. 24, 2026

(54) COMPUTED TOMOGRAPHY DEVICE AND METHOD FOR COVERING A REGION TO BE COVERED OF A GANTRY OF A COMPUTED TOMOGRAPHY DEVICE

(71) Applicant: Siemens Healthineers AG, Forchheim (DE)

(72) Inventors: Christoph Eichner, Erlangen (DE); Viktor Loewen, Sankt Augustin (DE); Hans-Juergen Mueller, Pretzfeld (DE)

(73) Assignee: Siemens Healthineers AG, Forchheim (DE)

( * ) Notice: Subject to any disclaimer, the term of this patent is extended or adjusted under 35 U.S.C. 154(b) by 149 days.

(21) Appl. No.: 18/476,589

(22) Filed: Sep. 28, 2023

(65) Prior Publication Data

US 2024/0108294 A1 Apr. 4, 2024

(30) Foreign Application Priority Data

Sep. 30, 2022 (EP) .................................... 22199183

(51) Int. Cl.
*A61B 6/03* (2006.01)
*A61B 6/00* (2006.01)

(52) U.S. Cl.
CPC ............ *A61B 6/035* (2013.01); *A61B 6/4435* (2013.01)

(58) Field of Classification Search
None
See application file for complete search history.

(56) References Cited

U.S. PATENT DOCUMENTS

| | | | | |
|---|---|---|---|---|
| 4,645,933 | A | 2/1987 | Gambini et al. | |
| 4,977,585 | A * | 12/1990 | Boyd | A61B 6/035 |
| | | | | 378/19 |
| 6,325,538 | B1 * | 12/2001 | Heesch | G21F 3/00 |
| | | | | 250/517.1 |
| 7,057,194 | B2 * | 6/2006 | Goldstein | A61B 6/107 |
| | | | | 250/515.1 |
| 7,099,427 | B2 * | 8/2006 | Cadwalader | A61B 6/4423 |
| | | | | 250/519.1 |
| 2009/0110152 | A1 * | 4/2009 | Manzke | A61B 6/4423 |
| | | | | 378/195 |
| 2018/0235552 | A1 | 8/2018 | Aoki et al. | |
| 2018/0249972 | A1 * | 9/2018 | Yifat | G01T 1/04 |
| 2022/0117566 | A1 * | 4/2022 | Yifat | A61B 6/107 |

FOREIGN PATENT DOCUMENTS

| | | | | |
|---|---|---|---|---|
| CN | 114098790 A | * | 3/2022 | ............. A61B 6/107 |
| WO | WO 2018098147 A1 | | 5/2018 | |

* cited by examiner

*Primary Examiner* — Marcus H Taningco
(74) *Attorney, Agent, or Firm* — Harness, Dickey & Pierce, P.L.C.

(57) ABSTRACT

A computed tomography device has a gantry having a first gantry part, a second gantry part and a flexible material sheet. The first gantry part has a rotor having a projection data acquisition system and is movably mounted, via a linear guiding arrangement, relative to the second gantry part such that the first gantry part is configured for translational movement relative to the second gantry part. The gantry has a tensioning apparatus for the flexible material sheet. The flexible material sheet has a covering section, wherein the covering section spans between the first gantry part and the second gantry part to cover a region of the gantry.

22 Claims, 4 Drawing Sheets

COMPUTED TOMOGRAPHY DEVICE AND METHOD FOR COVERING A REGION TO BE COVERED OF A GANTRY OF A COMPUTED TOMOGRAPHY DEVICE

CROSS-REFERENCE TO RELATED APPLICATION(S)

The present application claims priority under 35 U.S.C. § 119 to European Patent Application No. 22199183.9, filed Sep. 30, 2022, the entire contents of which is incorporated herein by reference.

FIELD

One or more example embodiments of the present invention relate to a computed tomography device. One or more example embodiments of the present invention further relate to a method for covering a region to be covered of a gantry of a computed tomography device.

BACKGROUND

In the case of a stationary computed tomography device, the gantry remains stationary relative to a surrounding area of the computed tomography device during the imaging examination, wherein an examination object is moved relative to the gantry. In specific situations, it can be advantageous if a scanning movement can be performed while the examination object rests relative to a surrounding area of the computed tomography device, in particular relative to an examination space. For this purpose, the projection data acquisition system of the computed tomography device moves in a translational manner relative to the surrounding area of the computed tomography device while projection data is acquired from an examination region of the examination object via the projection data acquisition system.

For this purpose, it is possible for example to provide that a first gantry part, which has the projection data acquisition system, is movably mounted via a linear guiding arrangement relative to a second gantry part. In particular, in the region of the linear guiding arrangement it can be required to cover a region of the gantry, for example in order to secure this against an intervention from the outside and/or to seal against contaminations, in particular against dust and/or fluids.

SUMMARY

An object of one or more example embodiments of the present invention is to provide an alternative to conventional solutions that relate to covering the region to be covered of a gantry of a computed tomography device. Each subject matter of an independent claim achieves at least this object. Further advantageous aspects of embodiments of the present invention are taken into consideration in the dependent claims.

One or more example embodiments of the present invention relate to a computed tomography device having a gantry having a first gantry part, a second gantry part and a flexible material sheet, wherein the first gantry part has a rotor having a projection data acquisition system and is movably mounted via a linear guiding arrangement relative to the second gantry part in such a manner that a translational movement of the first gantry part can be performed relative to the second gantry part, in particular can be performed along the linear guiding arrangement, characterized in that the gantry has a tensioning apparatus for the flexible material sheet and that the flexible material sheet has a covering section, wherein the covering section is spanned between the first gantry part and the second gantry part so as to cover a region to be covered of the gantry, in particular is spanned by the tensioning apparatus.

The linear guiding arrangement can have for example a rail system and/or a carriage system that works together with the rail system. In particular, it can be provided that the first gantry part has the carriage system and/or that the second gantry part has the rail system. In particular, it can be provided that the region that is to be covered comprises the linear guiding arrangement and/or the rail system.

Moreover, the gantry can have for example a linear drive for driving the translational movement of the first gantry part relative to the second gantry part. The linear drive can have for example a threaded spindle and a screw drive that works together with the threaded spindle. In particular, it can be provided that the first gantry part has the screw drive and/or that the second gantry part has the threaded spindle.

In particular, it can be provided that the region to be covered of the gantry comprises a region to be covered of the second gantry part and/or that the region to be covered of the gantry comprises a region to be covered of the first gantry part. In particular, it can be provided that the second gantry part has the region to be covered of the gantry.

The flexible material sheet can be designed for example as a textile and/or as a film, in particular a plastic film. The flexible material sheet can be designed in particular in the form of a flat strip. The flexible material sheet for example can be woven. The flexible material sheet can be for example impregnated and/or can have surfaces that repel contaminations. The flexible material sheet can be designed in particular in such a manner that it can be thoroughly cleaned with little effort.

One embodiment provides that the tensioning apparatus is configured so as to cause a change in length of the covering section, which follows the translational movement of the first gantry part relative to the second gantry part.

In particular, it can be provided that the first gantry part and the second gantry part are arranged relative to one another in such a manner that the translational movement of the first gantry part relative to the second gantry part causes a change in length of the region to be covered of the gantry.

In particular, it can be provided that the tensioning apparatus is configured so as to counteract a change of a tensile stress in the covering section, in particular to counteract in such a manner that the change in length of the covering section follows the translational movement of the first gantry part relative to the second gantry part without a fundamental change in tensile stress in the covering section.

One embodiment provides that the flexible material sheet has a retracted section, wherein a transition between the covering section and the retracted section is formed via the tensioning apparatus, wherein the change in length of the covering section occurs in that a part section of the flexible material sheet passes the transition between the covering section and the retracted section.

One embodiment provides that the tensioning apparatus has a winding apparatus that is configured for a winding movement of the flexible material sheet and/or that the change in length of the covering section accompanies the winding movement of the flexible material sheet. In particular, it can be provided that the change in length of the covering section occurs due to the winding movement of the flexible material sheet and/or that the retracted section has a section that is wound by the winding apparatus.

In particular, it can be provided that the second gantry part has the winding apparatus. The winding apparatus can have for example a shaft for the flexible material sheet and/or a tensioning element, for example in the form of a torsion spring. The tensioning element can exert for example a tensioning torque on the shaft in such a manner that a tensile stress is caused on the flexible material sheet. The winding apparatus and the flexible material sheet can work together for example in the manner of a roller and/or can work together in such a manner that the flexible material sheet is tightly stretched, however is not overstretched.

In particular, it can be provided that the covering section is shortened due to a winding of the flexible material sheet via the winding apparatus and/or that the covering section is lengthened due to an unwinding of the flexible material sheet via the winding apparatus.

The winding of the flexible material sheet via the winding apparatus can be driven for example via the tensioning element of the winding apparatus. The unwinding of the flexible material sheet via the winding apparatus can be driven for example by a tensile force that is exerted by the first gantry part and the second gantry part on the flexible material sheet and/or that exerts a tensile torque, which overcomes the tensioning torque, onto the shaft of the winding apparatus.

One embodiment provides that the tensioning apparatus is configured so as to press an edge region of the covering section toward the region to be covered of the gantry. The edge region of the covering section can be designed in particular on the transition between the covering section and the retracted section.

One embodiment provides that the tensioning apparatus has a first deflecting roller for the flexible material sheet, wherein the flexible material sheet is guided between the first deflecting roller and the region to be covered of the gantry, wherein the first deflecting roller, abutting an outer side of the flexible material sheet, deflects the flexible material sheet if the first gantry part is located in a first position region relative to the second gantry part, wherein the outer side of the flexible material sheet is remote from the region to be covered of the gantry.

In particular, it can be provided that the transition between the covering section and the retracted section is formed on the first deflecting roller and/or that the edge region of the covering section is formed on the first deflecting roller.

One embodiment provides that the roller axis of the first deflecting roller and the linear guiding arrangement are oriented essentially and/or substantially perpendicular with respect to one another.

One embodiment provides that the tensioning apparatus has a tensioning apparatus supporting structure, a pivot bearing and a pivot arm, wherein the pivot arm is pivotably mounted about a pivot axis via the pivot bearing relative to the tensioning apparatus supporting structure, wherein the roller axis of the first deflecting roller is essentially and/or substantially parallel to the pivot axis, wherein the first deflecting roller is arranged at a distance from the pivot axis on the pivot arm.

In particular, it can be provided that the tensioning apparatus has a spring element that is tensioned between the pivot arm and the tensioning apparatus supporting structure and exerts a torque on the pivot arm about the pivot axis relative to the tensioning apparatus supporting structure in such a manner that the first deflecting roller presses the flexible material sheet toward the region to be covered of the gantry if the first gantry part is located in a first position region relative to the second gantry part.

In particular, it can be provided that the spring element exerts the torque on the pivot arm about the pivot axis relative to the tensioning apparatus supporting structure in such a manner that the first deflecting roller presses the edge region of the covering section toward the region to be covered of the gantry if the first gantry part is located in a first position region relative to the second gantry part.

In particular, it can be provided that the first deflecting roller is pivotably mounted about the pivot axis via the pivot arm and the pivot bearing relative to the tensioning apparatus supporting structure.

One embodiment provides that the tensioning apparatus has a second deflecting roller for the flexible material sheet, wherein the flexible material sheet is guided between the first deflecting roller and the second deflecting roller, wherein the second deflecting roller, abutting an inner side of the flexible material sheet, deflects the flexible material sheet if the first gantry part is located in a second position region relative to the second gantry part, wherein the inner side of the flexible material sheet is facing the region to be covered of the gantry.

In particular, it can be provided that the flexible material sheet is guided between the first deflecting roller and the second deflecting roller in such a manner that a turn of the flexible material sheet occurs from the first deflecting roller to the second deflecting roller if the first gantry part passes a border between the first position region relative to the second gantry part and the second position region relative to the second gantry part.

In particular, it can be provided that the roller axis of the second deflecting roller and the linear guiding arrangement are oriented essentially perpendicular with respect to one another and/or that the roller axis of the second deflecting roller is essentially parallel to the roller axis of the first deflecting roller. In particular, it can be provided that the second deflecting roller is arranged at a distance from the pivot axis on the pivot arm and/or that the second deflecting roller is arranged between the first deflecting roller and the pivot axis.

In particular, a positive-locking stop can be provided on the tensioning apparatus supporting structure in order to secure the pivot arm against deflecting too far as a result of the torque, for example if the first gantry part is located in the second position region relative to the second gantry part, wherein the counter-pressure ceases from the side of the region that is to be covered.

In particular, it can be provided that the first gantry part during a first section of the translational movement of the first gantry part relative to the second gantry part is located in the first position region relative to the second gantry part and/or that the first gantry part during a second section of the translational movement of the first gantry part relative to the second gantry part is located in the second position region relative to the second gantry part. In particular, it can be provided that during the translational movement of the first gantry part relative to the second gantry part, the first gantry part passes the border between the first position region relative to the second gantry part and the second position region relative to the second gantry part.

One embodiment provides that a first end of the flexible material sheet is fastened to the first gantry part in such a manner that the first end of the flexible material sheet follows the translational movement of the first gantry part relative to the second gantry part, and/or that a second end of the flexible material sheet is fastened to the second gantry part in such a manner that during the translational movement of the first gantry part relative to the second gantry part the second end of the flexible material sheet rests relative to the second gantry part.

For example, the first gantry part can have the tensioning apparatus. In particular, it can be provided that the first gantry part has the winding apparatus and/or that the first gantry part has the tensioning apparatus supporting structure, the pivot bearing and the pivot arm. The first end of the flexible material sheet can be fastened for example to the tensioning apparatus, in particular to the winding apparatus, in particular to the shaft of the winding apparatus.

The second end of the flexible material sheet can be fastened for example to a cladding of the second gantry part, in particular can be bonded and/or clamped between two cladding parts.

One embodiment provides that the gantry has an opening, wherein the opening is designed in such a manner that an examination object can be introduced along a system axis of the gantry into the opening, and/or that the translational movement of the first gantry part relative to the second gantry part along the system axis. In particular, it can be provided that the linear guiding arrangement is oriented parallel to the system axis. In particular, it can be provided that the first gantry part is arranged in an essentially annular manner around the system axis.

In particular, it can be provided that the first gantry part has a rotary bearing and a gantry supporting structure and that the rotor is connected via the rotary bearing to the gantry supporting structure and is rotatably mounted relative to the gantry supporting structure about the system axis.

The examination object can be for example a body part, in particular a human or animal body part, or a phantom. The examination object can be in particular a head of a human. The computed tomography device can be designed in particular as a head computed tomography device and/or as a mobile computed tomography device.

One or more example embodiments of the present invention further relate to a method for covering a region to be covered of a gantry of a computed tomography device, wherein the gantry has a first gantry part, a second gantry part, a flexible material sheet and a tensioning apparatus for the flexible material sheet, the method comprising:

spanning a covering section of the flexible material sheet between the first gantry part and the second gantry part so as to cover a region to be covered of the gantry, and
    performing a translational movement of the first gantry part relative to the second gantry part, wherein the first gantry part has a rotor having a projection data acquisition system and is movably mounted via a linear guiding arrangement relative to the second gantry part.

One embodiment provides that a change in length of the covering section is caused by the tensioning apparatus, wherein the change in length of the covering section follows the translational movement of the first gantry part relative to the second gantry part. In particular, it can be provided that the tensioning apparatus counteracts a change of a tensile stress in the covering section.

One embodiment provides that a transition between the covering section and a retracted section of the flexible material sheet is formed via the tensioning apparatus, and/or that the change in length of the covering section occurs in that a part section of the flexible material sheet passes the transition between the covering section and the retracted section.

One embodiment provides that the change in length of the covering section occurs due to a winding movement of the flexible material sheet via a winding apparatus of the tensioning apparatus. One embodiment provides that an edge region of the covering section is pressed via the tensioning apparatus toward the region to be covered of the gantry.

One embodiment provides that the first gantry part has a rear side of a cladding of the gantry, wherein the rear side of the cladding of the gantry surrounds a rear side of the opening in an annular manner, and/or that the third gantry part has a front side of a cladding of the gantry, wherein the front side of the cladding of the gantry surrounds a front side of the opening in an annular manner.

Within the scope of embodiments of the present invention, it is possible for features that are described in relation to different embodiments of the present invention and/or different claim categories (method, use, apparatus, system, arrangement etc.) to be combined to form further embodiments of the present invention. For example, a claim that relates to an apparatus can also be developed using features that are described or claimed in relation to a method and vice versa. Functional features of a method in this case can be performed by accordingly designed physical components. The use of the indefinite article "a" or "an" does not rule out that the relevant feature can also be provided multiple times.

BRIEF DESCRIPTION OF THE DRAWINGS

The present invention is explained below with the aid of exemplary embodiments with reference to the attached figures. The representation in the figures is schematic, greatly simplified and not necessarily to scale.

DETAILED DESCRIPTION

Figure 1:
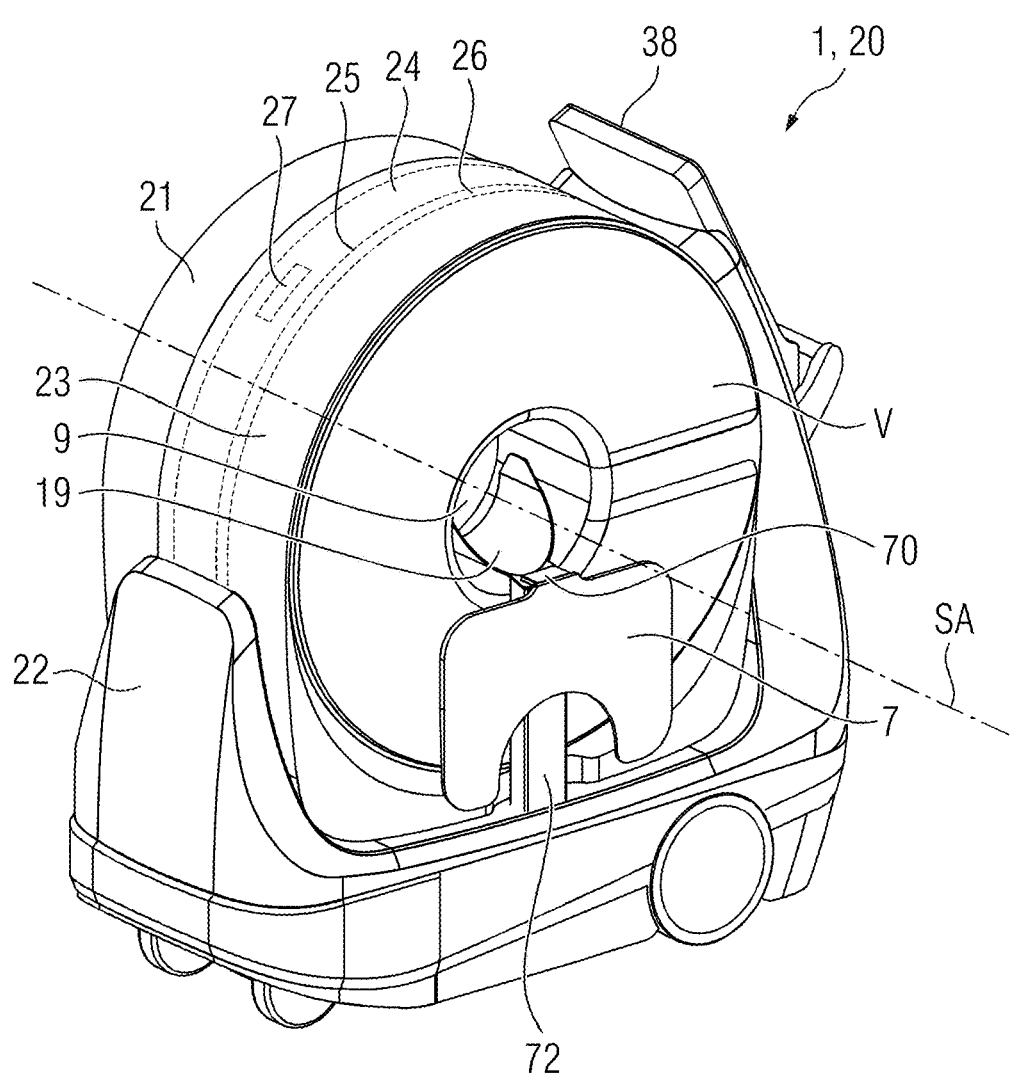
FIG. 1 shows a computed tomography device in the form of a mobile head computed tomography device having a head shell and a shoulder board.

FIG. 1 shows a computed tomography device 1 in the form of a mobile head computed tomography device having a head shell 19 and a shoulder board 7. The computed tomography device 1 has the gantry 20 having a first gantry part 21, a second gantry part 22 and a third gantry part 23, wherein the first gantry part 21 has a rotor 24 having a projection data acquisition system 27 and is movably mounted via a linear guiding arrangement relative to the second gantry part 22 in such a manner that a translational movement of the first gantry part 21 can be performed relative to the second gantry part 22, in particular can be performed along the linear guiding arrangement.

The first gantry part 21 has a rotary bearing 25 and a gantry supporting structure 26, wherein the rotor 24 is connected via the rotary bearing 25 to the gantry supporting structure 26 and is rotatably mounted relative to the gantry supporting structure 26 about the system axis SA. The second gantry part 22 has the holding apparatus 72. The holding apparatus 72 extends along the vertical direction Y. The shoulder board 7 is connected via the pivoting apparatus 70 to the holding apparatus 72 and is pivotably mounted relative to the gantry 20 about a pivot axis that is perpendicular to the system axis SA. The system axis SA is horizontal and parallel to the direction Z. The second gantry part 22 has a chassis for a horizontal transport movement of the gantry 20. The gantry 20 moreover has the touch-sensitive screen 38 for operating the computed tomography device 1.

The gantry 20 has an opening 9, wherein the opening 9 is designed in such a manner that an examination object can be introduced along a system axis SA of the gantry 20 into the opening 9, wherein the translational movement of the first gantry part 21 occurs relative to the second gantry part 22 along the system axis SA. In particular, it is provided that the first gantry part 21 is arranged in an essentially annular manner around the system axis SA and that the third gantry part 23 is arranged in an essentially annular manner around the system axis SA.

The first gantry part 21 has a rear side of a cladding V of the gantry 20, wherein the rear side of the cladding V of the gantry 20 surrounds a rear side of the opening 9 in an annular manner. The third gantry part 23 has a front side of a cladding V of the gantry 20, wherein the front side of the cladding V of the gantry 20 surrounds a front side of the opening 9 in an annular manner.

In addition to the illustrated flexible material sheet 8 that is arranged on the rear side of the gantry 20, it is possible for at least one further flexible material sheet to be arranged on the front side of the gantry 20. For example, for each of the two rails of the rail system 52 in each case a narrower flexible material sheet can be provided so as to cover the rails and in each case a smaller tensioning apparatus can be provided so as to span the corresponding narrower flexible material sheet that can be designed in particular in accordance with aspects that have been described in general for the flexible material sheet and the tensioning apparatus, in particular having a range of functions that deviate from the illustrated tensioning apparatus 84.

Figure 2:
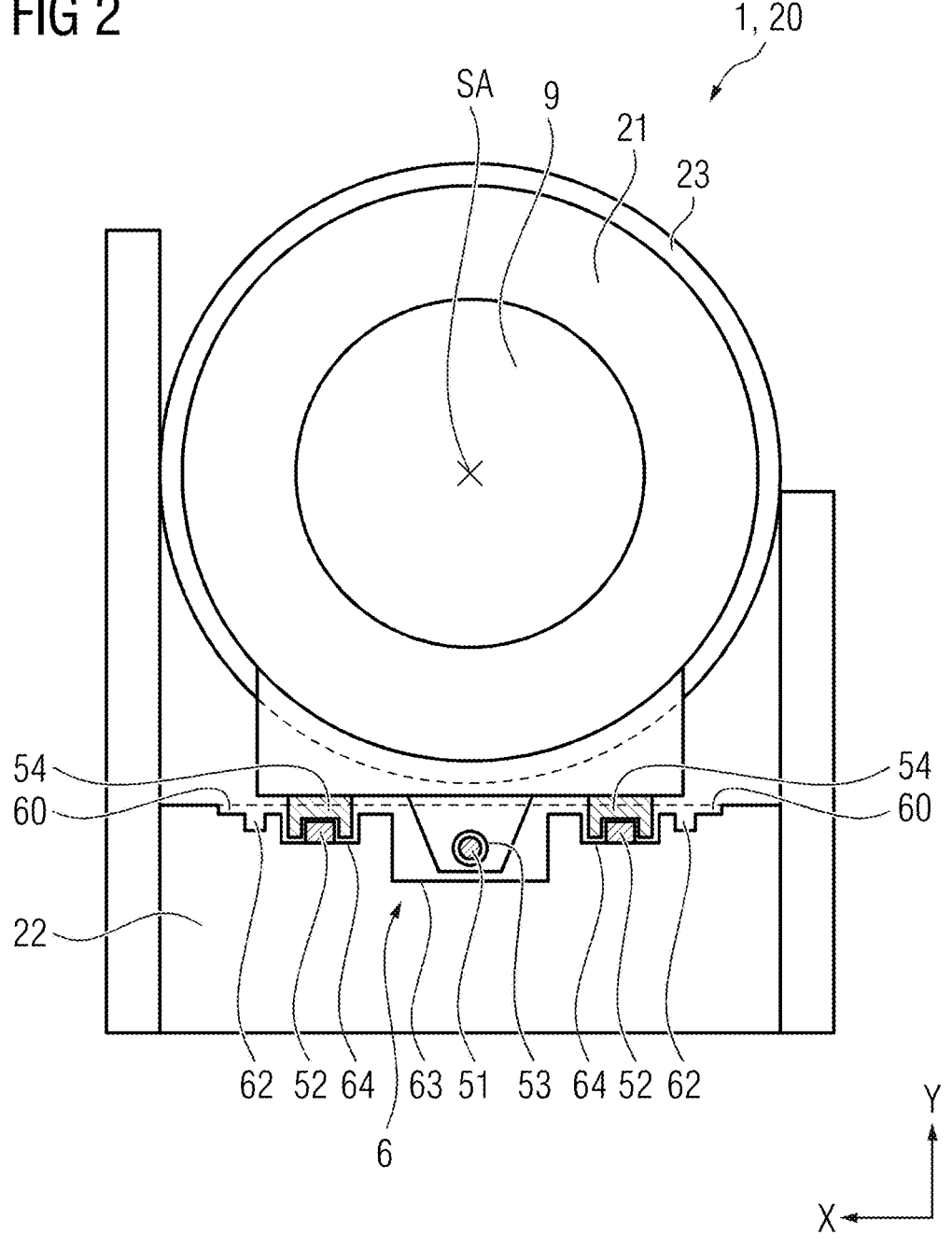
FIG. 2 shows a first view of the computed tomography device.

FIG. 2 shows a first view of the computed tomography device 1. The linear guiding arrangement has a rail system 52 and a carriage system 54 that works together with the rail system 52. In particular, it is provided that the first gantry part 21 has the carriage system 54 and that the second gantry part 22 has the rail system 52. In particular, it is provided that the region 6 that is to be covered comprises the linear guiding arrangement and thus the rail system 52.

Moreover, the gantry 20 has for example a linear drive for driving the translational movement of the first gantry part 21 relative to the second gantry part 22. The linear drive has for example a threaded spindle 51 and a screw drive 53 that works together with the threaded spindle 51. In particular, it is provided that the first gantry part 21 has the screw drive 53 and that the second gantry part 22 has the threaded spindle 51. In particular, it is provided that the region 6 to be covered of the gantry 20 comprises a region to be covered of the second gantry part 22. The region 6 that is to be covered comprises the depressions 64 for the linear guiding arrangement and a depression 63 for the linear drive.

Drainage channels 61, 62 are arranged in the region 6 to be covered in order to drain contaminants, in particular in the form of media that, despite the covering, enter into the region 6 to be covered. These contaminants can be guided out of the second gantry part 22 via the hose 66.

Figure 3:
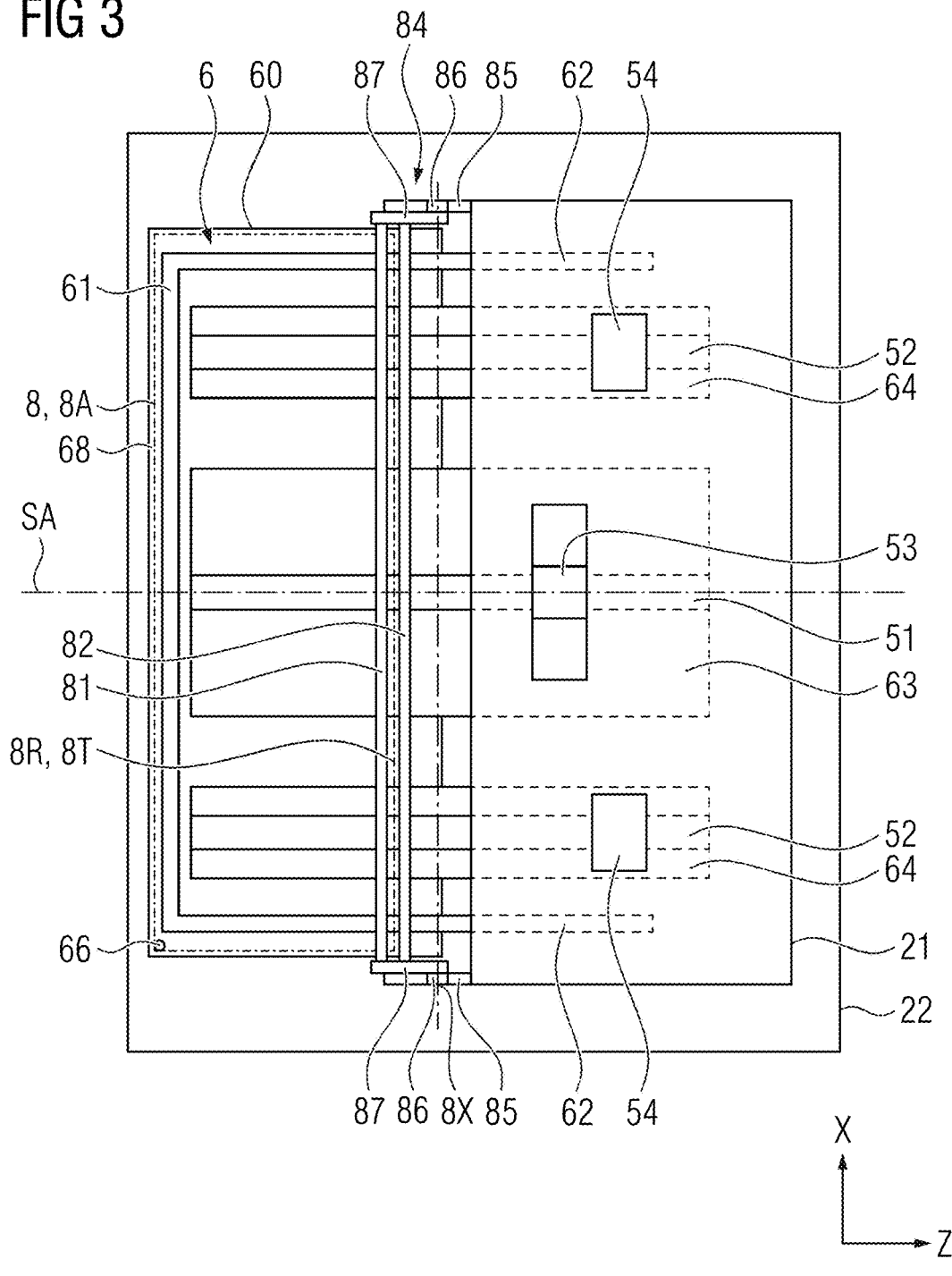
FIG. 3 shows a second view of the computed tomography device.

FIG. 3 illustrates a second view of the computed tomography device 1. The computed tomography device 1 has the gantry 20 having a first gantry part 21, a second gantry part 22 and a flexible material sheet 8, wherein the first gantry part 21 has a rotor 24 having a projection data acquisition system 27 and is movably mounted via a linear guiding arrangement relative to the second gantry part 22 in such a manner that a translational movement of the first gantry part 21 can be performed relative to the second gantry part 22, in particular can be performed along the linear guiding arrangement. The gantry 20 has a tensioning apparatus 84 for the flexible material sheet 8. The flexible material sheet 8 has a covering section 8A, wherein the covering section 8A is spanned between the first gantry part 21 and the second gantry part 22 so as to cover a region 6 to be covered of the gantry 20, in particular via the tensioning apparatus 84.

Figures 4, 5:
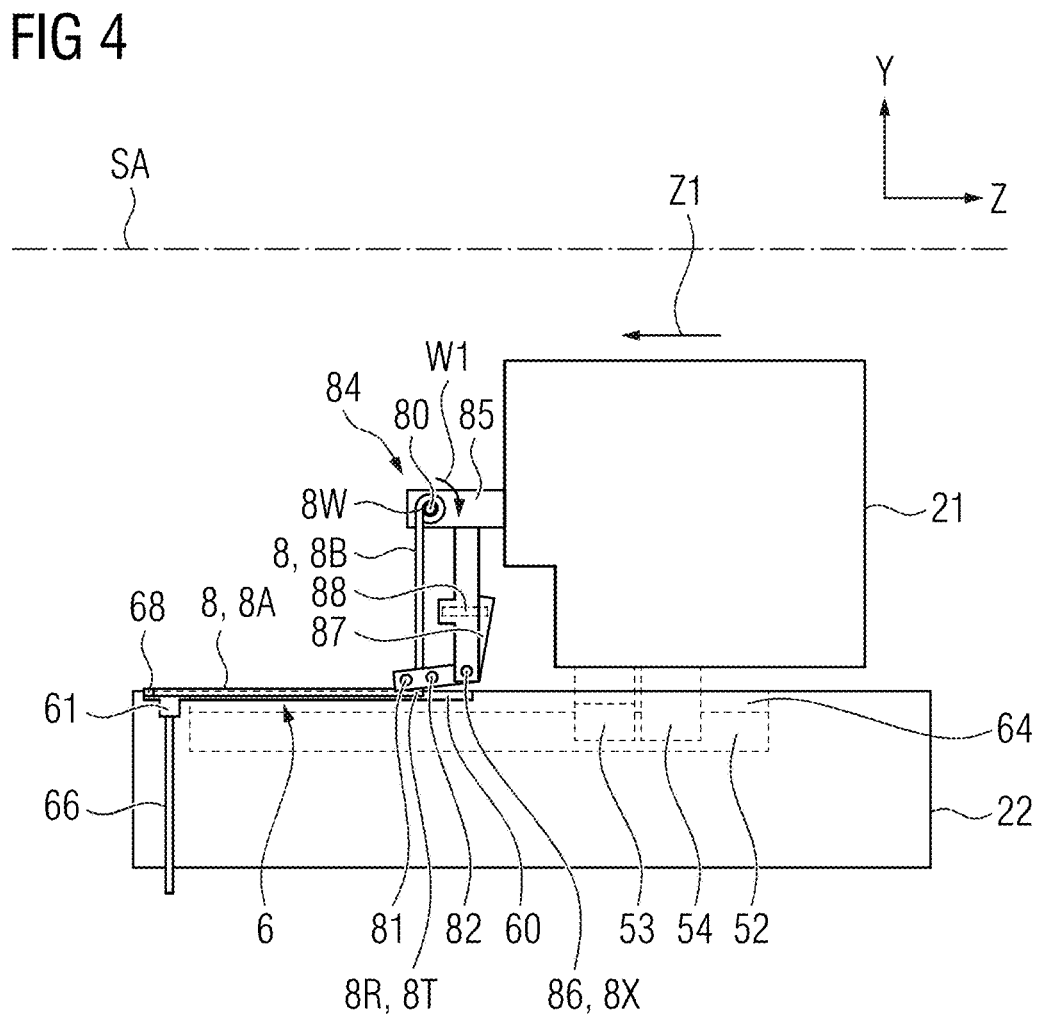
FIG. 4 shows a third view of the computed tomography device.
FIG. 5 shows a flowchart of a method for covering a region to be covered of a gantry of a computed tomography device.

FIG. 4 illustrates a third view of the computed tomography device 1. The tensioning apparatus 84 is configured so as to cause a change in length of the covering section 8A, which follows the translational movement of the first gantry part 21 relative to the second gantry part 22. The first gantry part 21 and the second gantry part 22 are arranged relative to one another in such a manner that the translational movement of the first gantry part 21 relative to the second gantry part 22 causes a change in length of the region 6 to be covered of the gantry 20.

The tensioning apparatus 84 is configured so as to counteract a change of a tensile stress in the covering section 8A, in particular to counteract in such a manner that the change in length of the covering section 8A follows the translational movement of the first gantry part 21 relative to the second gantry part 22 without a fundamental change in tensile stress in the covering section 8A.

The flexible material sheet 8 has a retracted section 8B, wherein a transition 8T between the covering section 8A and the retracted section 8B is formed via the tensioning apparatus 84, wherein the change in length of the covering section 8A occurs in that a part section of the flexible material sheet 8 passes the transition 8T between the covering section 8A and the retracted section 8B.

The tensioning apparatus 84 has a winding apparatus 80 that is configured for a winding movement of the flexible material sheet 8, wherein the change in length of the covering section 8A accompanies the winding movement of the flexible material sheet 8. The change in length of the covering section 8A occurs due to the winding movement of the flexible material sheet 8. The retracted section 8B has a section 8W that is wound via the winding apparatus 80.

The tensioning apparatus 84 is configured so as to press an edge region 8R of the covering section 8A toward the region 6 to be covered of the gantry 20. The edge region 8R of the covering section 8A is designed in particular on the transition 8T between the covering section 8A and the retracted section 8B.

The tensioning apparatus 84 has a first deflecting roller 81 for the flexible material sheet 8, wherein the flexible material sheet 8 is guided between the first deflecting roller 81 and the region 6 to be covered of the gantry 20, wherein the first deflecting roller 81, abutting an outer side of the flexible material sheet 8, deflects the flexible material sheet 8 if the first gantry part 21 is located in a first position region relative to the second gantry part 22, wherein the outer side of the flexible material sheet 8 is remote from the region 6 to be covered of the gantry 20.

The transition 8T between the covering section 8A and the retracted section 8B is formed on the first deflecting roller 81 and the edge region 8R of the covering section 8A is formed on the first deflecting roller 81. The roller axis of the first deflecting roller 81 and the linear guiding arrangement are oriented essentially perpendicular with respect to one another.

The tensioning apparatus 84 has a tensioning apparatus supporting structure 85, a pivot bearing 86 and a pivot arm 87, wherein the pivot arm 87 is pivotably mounted about a pivot axis 8X via the pivot bearing 86 relative to the tensioning apparatus supporting structure 85, wherein the roller axis of the first deflecting roller 81 is essentially parallel to the pivot axis 8X, wherein the first deflecting roller 81 is arranged at a distance from the pivot axis 8X on the pivot arm 87. The tensioning apparatus 84 has a spring element 88 that is tensioned between the pivot arm 87 and the tensioning apparatus supporting structure 85 and exerts a torque on the pivot arm 87 about the pivot axis 8X relative to the tensioning apparatus supporting structure 85 in such a manner that the first deflecting roller 81 presses the flexible material sheet 8 toward the region 6 to be covered of the gantry 20 if the first gantry part 21 is located in a first position region relative to the second gantry part 22.

The spring element 88 exerts the torque on the pivot arm 87 about the pivot axis 8X relative to the tensioning apparatus supporting structure 85 in such a manner that the first deflecting roller 81 presses the edge region 8R of the covering section 8A toward the region 6 to be covered of the gantry 20 if the first gantry part 21 is located in a first position region relative to the second gantry part 22. In particular, it is provided that the first deflecting roller 81 is pivotably mounted about the pivot axis 8X via the pivot arm 87 and the pivot bearing 86 relative to the tensioning apparatus supporting structure 85.

The tensioning apparatus 84 has a second deflecting roller 82 for the flexible material sheet 8, wherein the flexible material sheet 8 is guided between the first deflecting roller 81 and the second deflecting roller 82, wherein the second deflecting roller 82, abutting an inner side of the flexible material sheet 8, deflects the flexible material sheet 8 if the first gantry part 21 is located in a second position region relative to the second gantry part 22, wherein the inner side of the flexible material sheet 8 is facing the region 6 to be covered of the gantry 20.

In particular, it is provided that the flexible material sheet 8 is guided between the first deflecting roller 81 and the second deflecting roller 82 in such a manner that a turn of the flexible material sheet 8 occurs from the first deflecting roller 81 to the second deflecting roller 82 if the first gantry part 21 passes a border between the first position region relative to the second gantry part 22 and the second position region relative to the second gantry part 22.

The second position region relative to the second gantry part 22 follows in the direction Z1 the first position region relative to the second gantry part 21. The first deflecting roller 81 is located approximately over the connecting region 68 on the border between the first position region relative to the second gantry part 22 and the second position region relative to the second gantry part 22.

In particular, it is provided that the roller axis of the second deflecting roller 82 and the linear guiding arrangement are oriented essentially perpendicular with respect to one another and that the roller axis of the second deflecting roller 82 is essentially parallel to the roller axis of the first deflecting roller 81. In particular, it is provided that the second deflecting roller 82 is arranged at a distance from the pivot axis 8X on the pivot arm 87 and that the second deflecting roller 82 is arranged between the first deflecting roller 81 and the pivot axis 8X.

A first end of the flexible material sheet 8 is fastened to the first gantry part 21 in such a manner that the first end of the flexible material sheet 8 follows the translational movement of the first gantry part 21 relative to the second gantry part

22. A second end of the flexible material sheet 8 is fastened to the second gantry part 22 in such a manner that during the translational movement of the first gantry part 21 relative to the second gantry part 22 the second end of the flexible material sheet 8 rests relative to the second gantry part 22.

The first gantry part 21 has the tensioning apparatus 84. In particular, it is provided that the first gantry part 21 has the winding apparatus 80 and that the first gantry part 21 has the tensioning apparatus supporting structure 85, the pivot bearing 86 and the pivot arm 87. The first end of the flexible material sheet 8 is fastened to the tensioning apparatus 84, in particular to the winding apparatus 80, in particular to the shaft of the winding apparatus.

Consequently, the rail system 52 is covered via the covering section 8A in a space-saving manner, for example in order to seal against dust and media and also to protect against intervention. If the translational movement of the first gantry part 21 relative to the second gantry part 22 occurs in the direction Z1, the winding W1 of the flexible material sheet 8 via the winding apparatus 80 accompanies the translational movement. As a consequence, the covering section 8A is little by little removed from the trajectory of the translational movement so that the running of the carriage system 54 on the rail system 52 is not disturbed by the covering section 8A. If the translational movement of the first gantry part 21 relative to the second gantry part 22 occurs in the direction Z, an unwinding of the flexible material sheet 8 by the winding apparatus 80 accompanies the translational movement.

The covering section 8A is pressed via the tensioning apparatus 84 onto the second gantry part 22, in particular onto a cladding of the second gantry part 22. The second gantry part 22 has a step-shaped recessed support region 60 for the positive-locking receiving of the edges of the covering section 8A. The covering section 8A rolls from the first deflecting roller 81 flat into the step-shaped recessed support region 60. As a consequence, a gap between the covering section 8A and the covering region 6 is minimized whereby in particular the sealing effect and also the optical impression is improved.

The second end of the flexible material sheet 8 is fastened to the cladding of the second gantry part 22 along the connecting region 68. The connecting region 68 extends essentially perpendicular to the system axis SA.

FIG. 5 illustrates a flowchart of a method for covering a region 6 to be covered of a gantry 20 of a computed tomography device 1, wherein the gantry 20 has a first gantry part 21, a second gantry part 22, a flexible material sheet 8 and a tensioning apparatus 84 for the flexible material sheet 8, the method comprising:

spanning M1 a covering section 8A of the flexible material sheet 8 between the first gantry part 21 and the second gantry part 22 so as to cover a region 6 to be covered of the gantry 20, and performing M2 a translational movement of the first gantry part 21 relative to the second gantry part 22, wherein the first gantry part 21 has a rotor 24 having a projection data acquisition system 27 and is movably mounted via a linear guiding arrangement relative to the second gantry part 22.

A change in length of the covering section 8A is caused by the tensioning apparatus 84, wherein the change in length of the covering section 8A follows the translational movement of the first gantry part 21 relative to the second gantry part 22. In particular, it is provided that the tensioning apparatus 84 counteracts a change of a tensile stress in the covering section 8A.

A transition 8T between the covering section 8A and a retracted section 8B of the flexible material sheet 8 is formed by the tensioning apparatus 84, wherein the change in length of the covering section 8A occurs in that a part section of the flexible material sheet 8 passes the transition 8T between the covering section 8A and the retracted section 8B.

The change in length of the covering section 8A occurs due to a winding movement of the flexible material sheet 8 by a winding apparatus 80 of the tensioning apparatus 84. The edge region 8R of the covering section 8A is pressed by the tensioning apparatus 84 toward the region 6 to be covered of the gantry 20.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

What is claimed is:

1. A computed tomography device, comprising:
a gantry having a first gantry part, a second gantry part and a flexible material sheet, the first gantry part including a rotor having a projection data acquisition system, the first gantry part being movably mounted relative to the second gantry part via a linear guiding arrangement such that the first gantry part is configured for translational movement relative to the second gantry part, the gantry including a tensioning apparatus for the flexible material sheet, the flexible material sheet including a covering section spanning between the first gantry part and the second gantry part to cover a region of the gantry, and the tensioning apparatus being configured to cause a change in a length of the covering section corresponding to the translational movement of the first gantry part relative to the second gantry part.

2. The computed tomography device as claimed in claim 1, wherein
the flexible material sheet includes a retracted section;;
a transition between the covering section and the retracted section is formed by the tensioning apparatus; and
change in the length of the covering section corresponds to a section of the flexible material sheet passing the transition between the covering section and the retracted section.

3. The computed tomography device as claimed in claim 2, wherein
the tensioning apparatus includes a winding apparatus configured to wind the flexible material sheet; and
the change in the length of the covering section corresponds to winding of the flexible material sheet.

4. The computed tomography device as claimed in claim 1, wherein
the tensioning apparatus includes a winding apparatus configured to wind the flexible material sheet; and
the change in the length of the covering section corresponds to winding of the flexible material sheet.

5. The computed tomography device as claimed in claim 4, wherein the tensioning apparatus is configured to press an edge region of the covering section toward the region of the gantry.

6. The computed tomography device as claimed in claim 1, wherein the tensioning apparatus is configured to press an edge region of the covering section toward the region of the gantry.

7. The computed tomography device as claimed in claim 6, wherein
the tensioning apparatus includes a first deflecting roller;
the flexible material sheet is guided between the first deflecting roller and the region of the gantry;
the first deflecting roller, abuts an outer side of the flexible material sheet and deflects the flexible material sheet based on the first gantry part being located in a first position region relative to the second gantry part; and
the outer side of the flexible material sheet is remote from the region of the gantry.

8. The computed tomography device as claimed in claim 1, wherein
the tensioning apparatus includes a first deflecting roller;
the flexible material sheet is guided between the first deflecting roller and the region of the gantry;
the first deflecting roller abuts an outer side of the flexible material sheet and deflects the flexible material sheet based on the first gantry part being located in a first position region relative to the second gantry part; and the outer side of the flexible material sheet is remote from the region of the gantry.

9. The computed tomography device as claimed in claim 8,
wherein a roller axis of the first deflecting roller and the linear guiding arrangement are oriented substantially perpendicular with respect to one another.

10. The computed tomography device as claimed in claim 9, wherein
the tensioning apparatus includes a tensioning apparatus supporting structure, a pivot bearing and a pivot arm,;
the pivot arm is pivotably mounted about a pivot axis via the pivot bearing, the pivot arm being pivotably mounted relative to the tensioning apparatus supporting structure;
the roller axis of the first deflecting roller is substantially parallel to the pivot axis;
the first deflecting roller is at a distance from the pivot axis on the pivot arm; and
the tensioning apparatus includes a spring element that is tensioned between the pivot arm and the tensioning apparatus supporting structure, the spring element being configured to exert a torque on the pivot arm about the pivot axis relative to the tensioning apparatus supporting structure such that the first deflecting roller presses the flexible material sheet toward the region of the gantry based on the first gantry part being located in the first position region relative to the second gantry part.

11. The computed tomography device as claimed in claim 10, wherein
the tensioning apparatus includes a second deflecting roller;
the flexible material sheet is guided between the first deflecting roller and the second deflecting roller;
the second deflecting roller abuts an inner side of the flexible material sheet and deflects the flexible material sheet based on the first gantry part being located in a second position region relative to the second gantry part; and
the inner side of the flexible material sheet faces the region of the gantry.

12. The computed tomography device as claimed in claim 8, wherein
the tensioning apparatus includes a tensioning apparatus supporting structure, a pivot bearing and a pivot arm;;
the pivot arm is pivotably mounted about a pivot axis via the pivot bearing, the pivot arm being pivotably mounted relative to the tensioning apparatus supporting structure;
a roller axis of the first deflecting roller is substantially parallel to the pivot axis;
the first deflecting roller is t a distance from the pivot axis on the pivot arm; and
the tensioning apparatus includes a spring element that is tensioned between the pivot arm and the tensioning apparatus supporting structure, the spring element being configured to exert a torque on the pivot arm about the pivot axis relative to the tensioning apparatus supporting structure such that the first deflecting roller presses the flexible material sheet toward the region of the gantry based on the first gantry part being located in the first position region relative to the second gantry part.

13. The computed tomography device as claimed in claim 8, wherein the tensioning apparatus includes a second deflecting roller;

the flexible material sheet is guided between the first deflecting roller and the second deflecting roller,;

the second deflecting roller abuts an inner side of the flexible material sheet and deflects the flexible material sheet based on the first gantry part being located in a second position region relative to the second gantry part; and the inner side of the flexible material sheet faces the region of the gantry.

14. The computed tomography device as claimed in claim 1, wherein a first end of the flexible material sheet is fastened to the first gantry part such that the first end of the flexible material sheet follows the translational movement of the first gantry part relative to the second gantry part; and a second end of the flexible material sheet is fastened to the second gantry part such that during the translational movement of the first gantry part relative to the second gantry part the second end of the flexible material sheet is at rest relative to the second gantry part.

15. A method for covering a region of a gantry of a computed tomography device, the gantry having a first gantry part, a second gantry part, a flexible material sheet and a tensioning apparatus for the flexible material sheet, and the method comprising:

spanning a covering section of the flexible material sheet between the first gantry part and the second gantry part to cover the region of the gantry; and performing translational movement of the first gantry part relative to the second gantry part, the first gantry part including a rotor having a projection data acquisition system, the first gantry part being movably mounted relative to the second gantry part via a linear gliding arrangement, and the performing the translational movement including causing a change in a length of the covering section by the tensioning apparatus, the change in the length of the covering section corresponding to the translational movement.

16. The method as claimed in claim 1, wherein a transition between the covering section and a retracted section of the flexible material sheet is formed by the tensioning apparatus; and the change in the length of the covering section corresponds to a section of the flexible material sheet passing the transition between the covering section and the retracted section.

17. The method as claimed in claim 15, wherein the change in the length of the covering section corresponds to winding of the flexible material sheet via a winding apparatus of the tensioning apparatus.

18. The method as claimed in claim 15, wherein the performing the translational movement includes pressing an edge region of the covering section toward the region of the gantry by the tensioning apparatus.

19. A computed tomography device, comprising:

a gantry having a first gantry part, a second gantry part and a flexible material sheet, the first gantry part including a rotor having a projection data acquisition system, the first gantry part being movably mounted relative to the second gantry part via a linear guiding arrangement such that the first gantry part is configured for translational movement relative to the second gantry part, the gantry including a tensioning apparatus for the flexible material sheet, the flexible material sheet including a covering section spanning between the first gantry part and the second gantry part to cover a region of the gantry, and the tensioning apparatus being configured to press an edge region of the covering section toward the region of the gantry.

20. A computed tomography device, comprising:

a gantry having a first gantry part, a second gantry part and a flexible material sheet, the first gantry part including a rotor having a projection data acquisition system, the first gantry part being movably mounted relative to the second gantry part via a linear guiding arrangement such that the first gantry part is configured for translational movement relative to the second gantry part, the gantry including a tensioning apparatus for the flexible material sheet, the flexible material sheet including a covering section spanning between the first gantry part and the second gantry part to cover a region of the gantry, the tensioning apparatus including a first deflecting roller, the flexible material sheet being guided between the first deflecting roller and the region of the gantry, the first deflecting roller abutting an outer side of the flexible material sheet and deflecting the flexible material sheet based on the first gantry part being located in a first position region relative to the second gantry part, and the outer side of the flexible material sheet being remote from the region of the gantry.

21. A computed tomography device, comprising:

a gantry having a first gantry part, a second gantry part and a flexible material sheet, the first gantry part including a rotor having a projection data acquisition system, the first gantry part being movably mounted relative to the second gantry part via a linear guiding arrangement such that the first gantry part is configured for translational movement relative to the second gantry part, the gantry including a tensioning apparatus for the flexible material sheet, the flexible material sheet including a covering section spanning between the first gantry part and the second gantry part to cover a region of the gantry, a first end of the flexible material sheet being fastened to the first gantry part such that the first end of the flexible material sheet follows the translational movement of the first gantry part relative to the second gantry part, and a second end of the flexible material sheet being fastened to the second gantry part such that during the translational movement of the first gantry part relative to the second gantry part the second end of the flexible material sheet is at rest relative to the second gantry part.

22. A method for covering a region of a gantry of a computed tomography device, the gantry having a first gantry part, a second gantry part, a flexible material sheet and a tensioning apparatus for the flexible material sheet, and the method comprising:

spanning a covering section of the flexible material sheet between the first gantry part and the second gantry part to cover the region of the gantry; and performing translational movement of the first gantry part relative to the second gantry part, the first gantry part including a rotor having a projection data acquisition system, the first gantry part being movably mounted relative to the second gantry part via a linear gliding arrangement, and the performing the translational movement includes pressing an edge region of the covering section toward the region of the gantry by the tensioning apparatus.

* * * * *